(12) United States Patent
Adams et al.

(10) Patent No.: US 7,179,836 B2
(45) Date of Patent: Feb. 20, 2007

(54) CHEMICAL COMPOUNDS

(75) Inventors: Jerry Leroy Adams, King of Prussia, PA (US); Domingos J Silva, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 406 days.

(21) Appl. No.: 10/489,942

(22) PCT Filed: Sep. 20, 2002

(86) PCT No.: PCT/US02/29739

§ 371 (c)(1),
(2), (4) Date: Mar. 17, 2004

(87) PCT Pub. No.: WO03/027093

PCT Pub. Date: Apr. 3, 2003

(65) Prior Publication Data

US 2004/0192941 A1    Sep. 30, 2004

Related U.S. Application Data

(60) Provisional application No. 60/324,003, filed on Sep. 21, 2001.

(51) Int. Cl.
*A61K 31/38* (2006.01)
*C07D 333/36* (2006.01)
(52) U.S. Cl. .......................................... 514/447; 549/68
(58) Field of Classification Search .................. 549/68; 514/447

See application file for complete search history.

(56) References Cited

U.S. PATENT DOCUMENTS

| 5,422,335 | A | | 6/1995 | Hagen et al. |
| 6,143,777 | A | | 11/2000 | Jonas et al. |
| 6,660,732 | B2 | * | 12/2003 | Betageri et al. ......... 514/227.8 |
| 6,835,745 | B2 | * | 12/2004 | Coghlan et al. ............ 514/448 |
| 6,858,223 | B2 | * | 2/2005 | Hafner ...................... 424/434 |
| 6,881,741 | B2 | * | 4/2005 | Chan Chun Kong et al. . 514/91 |
| 7,019,027 | B2 | * | 3/2006 | Linden et al. .............. 514/447 |

FOREIGN PATENT DOCUMENTS

WO     WO 01/58890     8/2001

\* cited by examiner

*Primary Examiner*—Deborah C. Lambkin
(74) *Attorney, Agent, or Firm*—Loretta Sauermelch; James Kellerman; John L. Lemanowicz

(57) ABSTRACT

Thiophene derivatives are described herein. The described invention also includes methods of making such thiophene derivatives as well as methods of using the same in the treatment of diseases.

13 Claims, No Drawings

CHEMICAL COMPOUNDS

CROSS REFERENCES TO RELATED APPLICATIONS

This application is a National Stage Application filed under 35 U.S.C. § 371 of PCT/US02/29739, filed on Sep. 20, 2002, which claims priority of U.S. Provisional Application No. 60/324,003, filed Sep. 21, 2001.

BACKGROUND OF THE INVENTION

The present invention relates to thiophene derivatives, compositions and medicaments containing the same, as well as processes for the preparation and use of such compounds, compositions and medicaments. Such thiophene derivatives are useful in the treatment of diseases associated with inappropriate angiogenesis.

The process of angiogenesis is the development of new blood vessels, generally capillaries, from pre-existing vasculature. Angiogenesis is defined as involving: (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogenesis is also activated during wound healing, and at certain stages of the female reproductive cycle. Inappropriate angiogenesis has been associated with several disease states including various retinopathies; ischemic disease; atherosclerosis; chronic inflammatory disorders; and cancer. The role of angiogenesis in disease states is discussed, for instance, in Fan et al., Trends in Pharmacol. Sci. 16: 54–66; Shawver et al., DDT Vol. 2, No. 2 February 1997; Folkmann, 1995, Nature Medicine 1: 27–31; Colville-Nash and Scott, Ann. Rheum. Dis., 51, 919,1992; Brooks et al., Cell, 79, 1157, 1994; Kahlon et al., Can. J. Cardiol. 8, 60, 1992; Folkman, Cancer Biol, 3, 65, 1992; Denekamp, Br. J. Rad. 66, 181, 1993; Fidler and Ellis, Cell, 79, 185, 1994; O'Reilly et al., Cell, 79, 315, 1994; Ingber et al., Nature, 348, 555, 1990; Friedlander et al., Science, 270, 1500, 1995; Peacock et al., J. Exp. Med. 175, 1135, 1992; Peacock et al., Cell. Immun. 160, 178, 1995; and Taraboletti et al., J. Natl. Cancer Inst. 87, 293, 1995.

In cancer the growth of solid tumors has been shown to be angiogenesis dependent. (See Folkmann, J., J. Nat'l. Cancer Inst., 1990, 82, 4–6.) Consequently, the targeting of pro-angiogenic pathways is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate angiogenesis (Pinedo, H. M. et al. The Oncologist, Vol. 5, No. 90001, 1–2, April 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97–111; S. A. Courtneidge, Dev. Supp. 1, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401).

Three PTK receptors for VEGF have been identified: VEGFR-1 (Flt-1); VEGFR-2 (Flk-1 or KDR) and VEGFR-3 (Flt4). These receptors are involved in angiogenesis and participate in signal transduction (Mustonen, T. et al. J. Cell Biol. 1995, 129: 895–898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3–10, April 2000).

Angiopoieten 1 (Ang1), a ligand for the endothelium-specific receptor tyrosine kinase TIE-2 is a novel angiogenic factor (Davis et al., Cell, 1996, 87: 1161–1169; Partanen et al., Mol. Cell Biol., 12: 1698–1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al., Curr. Topics Microbiol. Immunol., 1999, 237: 159–172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al., Cell, 1998, 93: 661–664; Peters, K. G., Circ. Res., 1998, 83(3): 342–3; Suri et al., Cell 87, 1996: 1171–1180).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorder associated with inappropriate angiogenesis could be provided.

The present inventors have discovered novel thiophene compounds, which are inhibitors of TIE-2 kinase activity, VEGFR-2 kinase activity, or both TIE-2 kinase and VEGFR-2 kinase activity. Such thiophene derivatives are useful in the treatment of disorders, including cancer, associated with inappropriate angiogenesis.

BRIEF SUMMARY OF THE INVENTION

In one aspect of the present invention, there is provided a compound of Formula (I):

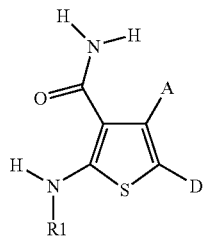

(I)

wherein:
A is aryl, heteroaryl, aryl or heteroaryl substituted with at least one independently selected $R^3$ group, heterocyclyl, —$RR^3$, —$C(O)OR^4$, —$C(O)NR^5R^6$, or —$C(O)R^4$;
D is hydrogen, $C_1$–$C_6$ alkyl, halo, aryl, heteroaryl, aryl or heteroaryl substituted with at least one independently selected $R^3$ group, heterocyclyl, —$RR^3$, —$C(O)OR^4$, —$C(O)NR^5R^6$, or —$C(O)R^4$;
R is $C_1$–$C_6$ alkylene, $C_2$–$C_6$ alkenylene, or $C_2$–$C_6$ alkynylene;
$R^1$ is hydrogen, $C_1$–$C_6$ alkyl, $C_3$–$C_7$ cycloalkyl, $C_1$–$C_6$ alkoxy, $C_3$–$C_7$ cycloalkoxy, aryl, aralkyl, aryloxy, heteroaryl, heterocyclyl, aryl or heteroaryl substituted with at least one independently selected $R^3$ group, —$C(O)OR^7$, or —$C(O)NR^7R^7$ (where both $R^7$ are not simultaneously H);
$R^3$ is halo, $C_1$–$C_6$ alkyl, $C_3$–$C_7$ cycloalkyl, $C_1$—$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —$NHC(O)R^4$, —$NHC(S)R^4$, —$NR^5R^6$, —$RNR^5R^6$, —$SR^4$, —$S(O)R^4$, —$S(O)_2R^4$, —$RC(O)OR^4$, —$C(O)OR^4$, —$C(O)R^4$, —$C(O)NR^5R^6$, —$NHS(O)_2R^4$, —$S(O)_2NR^5R^6$, or —$NHC(=NH)R^4$;
$R^4$ is hydrogen, $C_1$–$C_6$ alkyl, aryl, heteroaryl, heterocyclyl, —$RR^3$, —$NR'''R''''$, or —$NR'NR'''R''''$;
$R^5$ is hydrogen, $C_1$–$C_6$ alkyl, $C_3$–$C_7$ cycloalkyl, cyanoalkyl, —$R'R''$, aryl, aralkyl, heteroaryl, —$NHC(O)OR'''$, —$R'NHC(O)OR'''$, —$R'NHC(O)NR'''R''''$, or —$R'C(O)OR'''$;
$R^6$ is hydrogen, $C_1$–$C_6$ alkyl, $C_3$–$C_7$ cycloalkyl, cyanoalkyl, —$R'R''$, aryl, aralkyl, heteroaryl, —$C(O)OR'''$, or —$R'C(O)NR'''R'''$;
$R^7$ is hydrogen, $C_1$–$C_6$ alkyl, or aryl;
R' is $C_1$–$C_3$ alkylene;
R" is heteroalkyl or $NR'''R''''$;
R''' is hydrogen, $C_1$–$C_6$ alkyl, aryl, aralkyl, heteroaryl, or $C_3$–$C_7$ cycloalkyl; and
R'''' is hydrogen, $C_1$–$C_6$ alkyl, aryl, heteroaryl, or $C_3$–$C_7$ cycloalkyl;

or a salt, solvate, or physiologically functional derivative thereof.

In a second aspect of the invention, there is provided a compound of Formula (I) wherein A is aryl substituted with at least one independently selected $R^3$ group; and D, R, $R^1$, $R^3$, $R^4$, $R^5$, $R^6$, $R^7$, R', R", R''', and R'''' are as defined above; or a salt, solvate, or physiologically functional derivative thereof.

In a third aspect of the invention, there is provided a compound of Formula (I) wherein $R^1$ is hydrogen, and A, D, R, $R^3$, $R^4$, $R^5$, $R^6$, $R^7$, R', R", R''', and R'''' are as defined above; or a salt, solvate, or physiologically functional derivative thereof. In such compounds, A is preferably aryl substituted with at least one independently selected $R^3$ group.

In a fourth aspect of the present invention, there is provided a compound of Formula (I) wherein $R^1$ and D are both hydrogen, and A, R, $R^3$, $R^4$, $R^5$, $R^6$, $R^7$, R', R", R''', and R'''' are as defined above; or a salt, solvate, or physiologically functional derivative thereof. In such compounds, A is preferably aryl substituted with at least one independently selected $R^3$ group.

In a fifth aspect of the present invention, there is provided a pharmaceutical composition comprising a therapeutically effective amount of a compound of formula (I), or a salt, solvate, or a physiologically functional derivative thereof and one or more of pharmaceutically acceptable carriers, diluents and excipients.

In a sixth aspect of the present invention, there is provided a method of treating a disorder in a mammal, said disorder being mediated by at least one of inappropriate TIE-2 and VEGFR-2 activity, comprising: administering to said mammal a therapeutically effective amount of a compound of formula (I) or a salt, solvate or a physiologically functional derivative thereof.

In a seventh aspect of the present invention, there is provided a compound of formula (I), or a salt, solvate, or a physiologically functional derivative thereof for use in therapy.

In an eighth aspect of the present invention, there is provided the use of a compound of formula (I), or a salt, solvate, or a physiologically functional derivative thereof in the preparation of a medicament for use in the treatment of a disorder mediated by at least one of inappropriate TIE-2 and VEGFR-2 activity.

In a ninth aspect of the present invention, there is provided a method of treating a disorder in a mammal, said disorder being mediated by at least one of inappropriate TIE-2 and VEGFR-2 activity, comprising: administering to said mammal therapeutically effective amounts of (i) a compound of formula (I), or a salt, solvate or physiologically functional derivative thereof and (ii) an agent to inhibit growth factor receptor function.

In a tenth aspect of the present invention, there is provided a method of treating a disorder in a mammal, said disorder being characterized by inappropriate angiogenesis, comprising: administering to said mammal a therapeutically effective amount of a compound of formula (I), or a salt, solvate or physiologically functional derivative thereof.

DETAILED DESCRIPTION

All documents cited or referred to herein, including issued patents, published and unpublished patent applications, and other publications are hereby incorporated herein by reference as though fully set forth.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the numbering of the 2-amino-3-carboxamido-thiophene scaffold in formula (I) is assigned as shown in the structure following.

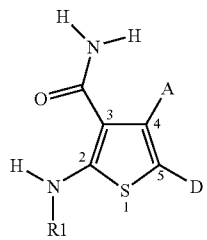

As used herein, the term "alkyl" refers to a straight or branched chain hydrocarbon radical having from one to twelve carbon atoms, optionally substituted with substituents selected from the group which includes $C_1$–$C_6$ alkyl, $C_1$–$C_6$ hydroxyalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aryl, aryloxy, heteroaryl, aminosulfonyl optionally substituted by alkyl or aryl, nitro, cyano, halogen, or $C_1$–$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$–$C_6$ alkyl" refers to an alkyl group as defined above containing at least 1, and at most 6, carbon atoms. Examples of branched or straight chained "$C_1$–$C_6$ alkyl" groups useful in the present invention include, but are not limited to, methyl, ethyl, n-propyl, isopropyl, isobutyl, n-butyl, t-butyl, n-pentyl, and isopentyl.

As used herein, the term "alkylene" refers to a straight or branched chain divalent hydrocarbon radical having from one to ten carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkylene" as used herein include, but are not limited to, methylene, ethylene, n-propylene, n-butylene, and the like.

As used herein, the terms "$C_1$–$C_6$ alkylene" and "$C_1$–$C_3$ alkylene" refer to an alkylene group, as defined above, which contains at least 1, and, respectively, at most 6 or at most 3, carbon atoms. Examples of "$C_1$–$C_3$ alkylene" groups useful in the present invention include, but are not limited to, methylene, ethylene, and n-propylene.

As used herein, the term "alkenyl" refers to a straight or branched chain hydrocarbon radical having from two to ten carbons and at least one carbon-carbon double bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkenyl" as used herein include ethenyl, propenyl, 1-butenyl, 2-butenyl, and isobutenyl.

As used herein, the term "$C_2$–$C_6$ alkenyl" refers to an alkenyl group as defined above containing at least 2, and at most 6, carbon atoms. Examples of "$C_2$–$C_6$ alkenyl" groups useful in the present invention include, but are not limited to, ethenyl, propenyl, 1-butenyl, 2-butenyl, and isobutenyl.

As used herein, the term "alkenylene" refers to a straight or branched chain divalent hydrocarbon radical having from two to ten carbon atoms and one or more carbon-carbon double bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the terms "$C_2$–$C_6$ alkenylene" and "$C_2$–$C_3$ alkenylene" refer to an alkenylene group as defined above containing at least 2, and, respectively, at most 6 or at most 3 carbon atoms. Examples of "$C_2$–$C_3$ alkenylene" groups useful in the present invention include, but are not limited to, ethene-1,2-diyl, propene-1,3-diyl, methylene-1,1-diyl, and the like.

As used herein, the term "alkynyl" refers to a straight or branched chain hydrocarbon radical having from two to ten carbons and at least one carbon-carbon triple bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, aryl, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkynyl" as used herein, include but are not limited to acetylenyl, 1-propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon-carbon triple bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Examples of "alkynylene" as used herein include, but are not limited to, ethyne-1,2-diyl, propyne-1,3-diyl, and the like.

As used herein, the terms "$C_2$–$C_6$ alkynylene" and "$C_2$–$C_3$ alkynylene" refers to an alkynylene group as defined above containing at least 2, and, respectively, at most 6 carbon atoms or at most 3 carbon atoms. Examples of "$C_2$–$C_3$ alkynylene" groups useful in the present invention include, but are not limited to, ethyne-1,2-diyl, propyne-1,3-diyl, and the like.

As used herein, the term "halogen" refers to fluorine (F), chlorine (Cl), bromine (Br), or iodine (I) and the term "halo" refers to the halogen radicals fluoro, chloro, bromo, and iodo.

As used herein, the term "$C_1$–$C_6$ haloalkyl" refers to an alkyl group as defined above containing at least 1, and at most 6, carbon atoms substituted with at least one halo group, halo being as defined herein. Examples of branched or straight chained "$C_1$–$C_6$ haloalkyl" groups useful in the present invention include, but are not limited to, methyl, ethyl, propyl, isopropyl, isobutyl and n-butyl substituted independently with one or more halos, e.g., fluoro, chloro, bromo and iodo, e.g., trifluoromethyl.

As used herein, the term "$C_3$–$C_7$ cycloalkyl" refers to a non-aromatic cyclic hydrocarbon radical having from three to seven carbon atoms and which optionally includes a $C_1$–$C_6$ alkyl linker through which it may be attached, and which is optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, $C_1$–$C_6$ perfluoroalkyl, multiple degrees of substitution being allowed. The $C_1$–$C_6$ alkyl group is as defined above. Exemplary "$C_3$–$C_7$ cycloalkyl" groups include, but are not limited to, cyclopropyl, cyclobutyl, cyclopentyl, cyclohexyl and cycloheptyl.

As used herein, the term "$C_3$–$C_7$ cycloalkylene" refers to a divalent non-aromatic cyclic hydrocarbon radical having from three to seven carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, $C_1$–$C_6$ perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered ring containing one or more heteroatomic substitutions selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen, or $C_1$–$C_6$ perfluoroalkyl, multiple degrees of substitution being allowed. Such a ring can be saturated or have one or more degrees of saturation. Such a ring may be optionally fused to one or more other optionally substituted, "heterocyclic" ring(s), aryl rings (including benzene rings), heteroaryl rings, or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to an unsaturated three to twelve-membered ring diradical containing one or more heteroatoms selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, carbamoyl optionally substituted by alkyl or aryl, aminosulfonyl optionally substituted by alkyl or aryl, nitro, cyano, halogen and $C_1$–$C_6$ perfluoroalkyl, multiple degrees of substitution being allowed. Such a ring has one or more degrees of unsaturation. Such a ring may be optionally fused to one or more optionally substituted aryl rings (including benzene rings), heterocyclic rings, heteroaryl rings, or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to an optionally substituted benzene ring or to an optionally substituted benzene ring fused to one or more optionally substituted benzene rings to form a ring system. Exemplary optional substituents include $C_1$–$C_6$ alkyl, $C_1$–$C_6$ alkoxy, $C_1$–$C_6$ haloalkyl, $C_1$–$C_6$ haloalkoxy, $C_1$–$C_6$ alkylsulfanyl, $C_1$–$C_6$ alkylsulfenyl, $C_1$–$C_6$ alkylsulfonyl, $C_1$–$C_6$ alkylsulfonylamino, arylsulfonylamino, alkylcarboxy, alkylcarboxamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halogen, heteroaryl, heterocyclyl, aryl optionally substituted with aryl, halogen, $C_1$–$C_6$ alkyl, $C_1$–$C_6$ haloalkyl, or $C_1$–$C_6$ alkylsulfonyl, ureido, arylurea, alkylurea, cycloalkylurea, alkylthiourea, aryloxy, or aralkoxy, multiple degrees of substitution being allowed. Such a ring or ring system may be optionally fused to one or more optionally substituted aryl rings (including benzene rings) or cycloalkyl rings. Examples of "aryl" groups include, but are not limited to, phenyl, 2-naphthyl, tetrahydronaphthyl, 1-naphthyl, biphenyl, indanyl, anthracyl, phenanthryl, or napthyl, as well as substituted derivatives thereof.

As used herein, the term "arylene" refers to an optionally substituted benzene ring diradical or to a benzene ring system diradical containing an optionally substituted benzene ring fused to one or more optionally substituted benzene rings. Exemplary optional substituents are selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl or aryl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl and aryl, multiple degrees of substitution being allowed. Such a ring or ring system may be optionally fused to one or more optionally substituted aryl rings (including benzene rings), or cycloalkyl rings. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a $C_1$–$C_3$ alkylene linker, wherein the $C_1$–$C_3$ alkylene is as defined herein. Examples of "aralkyl" include, but are not limited to, benzyl, phenylpropyl, 2-pyridylmethyl, 3-isoxazolylmethyl, 3-(1-methyl-5-t-butyl-pyrazyl)methyl, 3-isoxazolylmethyl, and 2-imidazoyly ethyl.

As used herein, the term "heteroaryl" refers to an optionally substituted monocyclic five to seven membered aromatic ring containing one or more heteroatomic substitutions selected from S, SO, $SO_2$, O, N, or N-oxide, or to such an aromatic ring fused to one or more, optionally substituted, such heteroaryl rings, aryl rings (including benzene rings), heterocyclic rings, or cycloalkyl rings (e.g., a bicyclic or tricyclic ring system). Examples of optional substituents are selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. Examples of "heteroaryl" groups used herein include, but are not limited to, furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" refers to a five- to seven-membered monocyclic aromatic diradical, or to a polycyclic aromatic diradical, containing one or more heteroatomic substitutions selected from S, SO, $SO_2$, O, N, or N-oxide, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl or aryl, carboxy, tetrazolyl, carbamoyl optionally substituted by alkyl or aryl, aminosulfonyl optionally substituted by alkyl or aryl, acyl, aroyl, heteroaroyl, acyloxy, aroyloxy, heteroaroyloxy, alkoxycarbonyl, nitro, cyano, halogen, $C_1$–$C_6$ perfluoroalkyl, heteroaryl, or aryl, multiple degrees of substitution being allowed. For polycyclic aromatic system diradicals, one or more of the rings may contain one or more heteroatoms, and one or more of the rings may be aryl, heterocyclic, heteroaryl, or cycloalkyl. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is alkyl as defined above and the term "$C_1$–$C_6$ alkoxy" refers to an alkoxy group as defined herein wherein the alkyl moiety contains at least 1, and at most 6, carbon atoms. Exemplary $C_1$–$C_6$ alkoxy groups useful in the present invention include, but are not limited to, methoxy, ethoxy, n-propoxy, isopropoxy, n-butoxy, and t-butoxy.

As used herein the term "aralkoxy" refers to the group $R_bR_aO$—, where $R_a$ is alkyl and $R_b$ is aryl as defined above.

As used herein the term "aryloxy" refers to the group $R_aO$—, where $R_a$ is aryl as defined above.

As used herein the term "ureido" refers to the group —$NHC(O)NH_2$.

As used herein, the term "arylurea" refers to the group —$NHC(O)NHR_a$ wherein $R_a$ is aryl as defined above.

As used herein, the term "arylthiourea" refers to the group —$NHC(S)NHR_a$ wherein $R_a$ is aryl as defined above.

As used herein, the term "alkylurea" refers to the group —$NHC(O)NHR_a$ wherein $R_a$ is alkyl as defined above.

As used herein, the term "cycloalkylurea" refers to the group —$NHC(O)NHR_a$ wherein $R_a$ is cycloalkyl as defined above.

As used herein, the term "$C_3$–$C_7$ cycloalkoxy" refers to the group $R_aO$—, where $R_a$ is $C_3$–$C_7$ cycloalkyl as defined above. Exemplary $C_3$–$C_7$ cycloalkoxy groups useful in the present invention include, but are not limited to cyclopropoxy, cyclobutoxy, and cyclopentoxy.

As used herein, the term "haloalkoxy" refers to the group $R_aO$—, where $R_a$ is haloalkyl as defined above and the term "$C_1$–$C_6$ haloalkoxy" refers to a haloalkoxy group as defined herein wherein the haloalkyl moiety contains at least 1, and at most 6, carbon atoms. Exemplary $C_1$–$C_6$ haloalkoxy groups useful in the present invention include, but is not limited to, trifluoromethoxy.

As used herein, the term "alkylsulfanyl" refers to the group $R_aS$—, where $R_a$ is alkyl as defined above and the term "$C_1$–$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS$—, where $R_a$ is haloalkyl as defined above and the term "$C_1$–$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$–$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$–$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —$NHS(O)_2R_a$ wherein $R_a$ is alkyl as defined above and the term "$C_1$–$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —$NHS(O)_2R_a$ wherein $R_a$ is aryl as defined above.

As used herein, the term "alkylcarboxyamide" refers to the group —$NHC(O)R_a$ wherein $R_a$ is alkyl, amino, or amino substituted with alkyl, aryl or heteroaryl as described above.

As used herein the term "alkylcarboxy" refers to the group —$C(O)R_a$ wherein $R_a$ is alkyl as described above.

As used herein, the term "oxo" refers to the group =O.

As used herein, the term "mercapto" refers to the group —SH.

As used herein, the term "carboxy" refers to the group —C(O)OH.

As used herein, the term "cyano" refers to the group —CN.

As used herein the term "cyanoalkyl" refers to the group —$R_aCN$, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —$S(O)_2NH_2$.

As used herein, the term "carbamoyl" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group R$_a$C(O)—, where R$_a$ is alkyl, cycloalkyl, or heterocyclyl as defined herein.

As used herein, the term "aroyl" refers to the group R$_a$C(O)—, where R$_a$ is aryl as defined herein.

As used herein, the term "aroylamino" refers to the group R$_a$C(O)NH—, where R$_a$ is aryl as defined herein.

As used herein, the term "heteroaroyl" refers to the group R$_a$C(O)—, where R$_a$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group R$_a$C(O)O—, where R$_a$ is alkyl, cycloalkyl, or heterocyclyl as defined herein.

As used herein, the term "aroyloxy" refers to the group R$_a$C(O)O—, where R$_a$ is aryl as defined herein.

As used herein, the term "heteroaroyloxy" refers to the group R$_a$C(O)O—, where R$_a$ is heteroaryl as defined herein.

As used herein, the term "optionally" means that the subsequently described event(s) may or may not occur, and includes both event(s) which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of formula (I) are included within the scope of the compounds of formula (I).

It is to be understood that reference to compounds of formula (I) herein refers to all compounds within the scope of formula (I) as defined above with respect to A, D, R, R$^1$, R$^3$, R$^4$, R$^5$, R$^6$, R$^7$, R', R", R''', or R'''' unless specifically limited otherwise.

Specific examples of compounds of the present invention include the following:

2-Amino-4-{4-[3-(2-fluoro-5-trifluoromethyl-phenyl)-ureido]-phenyl}-thiophene-3-carboxylic acid amide;

2-Amino-4-[4-(3-phenyl-ureido)-phenyl]-thiophene-3-carboxylic acid amide;

2-Amino-4-[4-[3-(2-chloro-5-trifluoromethyl-phenyl)-ureido]-phenyl]-thiophene-3-carboxylic acid amide;

2-Amino-4-[4-(3-indan-5-yl-ureido)-phenyl]-thiophene-3-carboxylic acid amide;

2-Amino-4-{4-[(1-[2-fluoro-5-trifluoromethyl-phenyl]-methanoyl)-amino]-phenyl}-thiophene-3-carboxylic acid amide;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and/or salts, solvates and/or physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

For example, pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating comprising a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 1986, 3(6): 318.

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes. Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to herein.

The compounds of the present invention and their salts and solvates, and physiologically functional derivatives thereof, may be employed alone or in combination with other therapeutic agents for the treatment of the conditions mentioned herein. In particular, in anti-cancer therapy, combination with other chemotherapeutic, hormonal or antibody agents is envisaged as well as combination with surgical therapy and/or radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds, or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula (I) include the following:

(1) cell cycle specific anti-neoplastic agents include, but are not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, topotecan, CPT-11 and the various optical forms of 7-(4-methylpiperazinomethylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are active as inhibitors of at least one of the protein kinases TIE-2 and VEGFR-2.

The present invention thus also provides compounds of formula (I) and pharmaceutically acceptable salts or solvates thereof, or physiologically functional derivatives thereof, for use in medical therapy, and particularly in the treatment of disorders mediated by at least one of inappropriate TIE-2 and VEGFR-2 kinase activity.

The inappropriate TIE-2 and/or VEGFR-2 activity referred to herein is any TIE-2 and/or VEGFR-2 activity that deviates from the normal TIE-2 and/or VEGFR-2 activity expected in a particular mammalian subject. Inappropriate TIE-2 and/or VEGFR-2 activity may take the form of, for instance, an abnormal increase in activity, or an aberration in the timing and or control of TIE-2 and/or VEGFR-2 activity. Such inappropriate activity may result then, for example, from overexpression or mutation of the protein kinase leading to inappropriate or uncontrolled activation. Furthermore, it is also understood that unwanted TIE-2 and/or VEGFR-2 activity may reside in an abnormal source, such as a malignancy. That is, the level of TIE-2 and/or VEGFR-2 activity does not have to be abnormal to be considered inappropriate, rather the activity derives from an abnormal source.

In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2 and/or VEGFR-2 for the prevention and/or treatment of disorders related to inappropriate TIE-2 and/or VEGFR-2 activity.

In particular, the compounds of the present invention are useful in the treatment of susceptible forms of cancer, including tumor growth and metastatis. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability, including blood vessel proliferative disorders including arthritis and restenosis; fibrotic disorders including hepatic cirrhosis and atherosclerosis; mesangial cell proliferative disorders including glomerulonephritis, diabetic nephropathy, malignant nephrosclerosis, thrombotic microangiopathy syndromes, organ transplant rejection and glomerulopathies; metabolic disorders including psoriasis, diabetes mellitus, chronic wound healing, inflammation and neurodegenerative diseases; also diabetic retinopathy; macular degeneration; other diseases characterized by ocular neovascularization; and diseases characterized by hemangiomas.

A further aspect of the invention provides a method of treatment of a mammal suffering from a disorder mediated by at least one of inappropriate TIE-2 and VEGFR-2 activity, which includes administering to said subject an effective amount of a compound of formula (I) or a pharmaceutically acceptable salt, solvate, or a physiologically functional derivative thereof. In a preferred embodiment, the disorder is cancer, e.g., malignant tumors. This aspect of the invention also provides such a method wherein the disorder is a disease afflicting mammals which are characterized by cellular proliferation in the area of disorders associated with neo-vascularization and/or vascular permeability, including those disclosed herein.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by at least one of inappropriate TIE-2 and VEGFR-2 activity. In a preferred embodiment, the disorder is cancer, e.g., malignant tumors.

This aspect of the invention also provides such a use wherein the disorder is a disease afflicting mammals which are characterized by cellular proliferation in the area of disorders associated with neo-vascularization and/or vascular permeability, including those disclosed herein.

A further aspect of the present invention provides the use of a compound of formula (I), or a pharmaceutically acceptable salt or solvate thereof, or a physiologically functional derivative thereof, in the preparation of a medicament for the treatment of cancer, e.g., malignant tumors.

The mammal requiring treatment with a compound of the present invention is typically a human being.

In another embodiment, therapeutically effective amounts of (a) the compounds of formula (I) or salts, solvates or physiologically derived derivatives thereof, and (b) agents which inhibit growth factor receptor function, may be administered in combination to a mammal for treatment of a disorder mediated by at least one of inappropriate TIE-2 and VEGFR-2 activity, for instance in the treatment of cancer, e.g., malignant tumors. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6):803–818 and in Shawver et al DDT Vol 2, No. 2 February 1997.

The compounds of the formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds, or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to at least one of inappropriate VEGFR2 and TIE-2 activity. In a further embodiment, the method further includes administering a therapeutically effective amount of a VEGFR2 inhibitor along with the compounds of formula (I) or salts, solvates or physiologically functional derivatives thereof. Preferably the disorder is cancer, e.g., malignant tumors. This aspect of the invention also provides such methods wherein the disorder is a disease afflicting mammals which are characterized by cellular proliferation in the area of disorders associated with neo-vascularization and/or vascular permeability, including those disclosed herein.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to at least one of inappropriate VEGFR2 and TIE-2 activity. In a further embodiment, the use further includes use of a VEGFR2 inhibitor to prepare said medicament. Preferably the disorder is cancer, e.g., malignant tumors. This aspect of the invention also provides such uses wherein the disorder is a disease afflicting mammals which are characterized by cellular proliferation in the area of disorders associated with neo-vascularization and/or vascular permeability, including those disclosed herein.

The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds, or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (I) can be prepared according to the synthetic sequences illustrated in Schemes 1 and 2, starting with the methylketone (i), which is here exemplified with, but should not be seen as limited to, a phenyl substituted ketone. The index "a" represent any number of optionally chosen substitutents, which may include any protective group(s) or any disguised group(s). Scheme 1 shows general routes for the synthesis of the targeted 2-amino-3-carboxamido-thiophene scaffold (iv). Specific detail of synthetic routes according to Schemes 1 and 2 is shown in the Examples following, wherein, for example, a 2-amino-3-carboxamido-thiophene compound having TIE-2 kinase inhibitory activity was prepared.

The synthesis of the 2-amino-3-carboxamido-thiophene scaffold (iv) containing a hydrogen group at C-5 is illustrated in Scheme 1. The ring system (iv) can be assembled in one-step from the methyl ketone (i), as adapted from a procedure published for 2-amino-3-carboxamido-5-phenyl-thiophene scaffolds: Beecham Group Limited, U.S. Pat. No. 3,963,750. The same ring system (iv) can be assembled in a three-step procedure from (i), where the intermediate 2-amino-3-cyano-thiophene (iii) is hydrolyzed to the desired amide: Schaefer, H., et al., J. Prakt. Chem., 1984, 326, N6, 917–923. Both pathways may serve as routes to produce various derivatives starting from methylketones (i).

As shown in Scheme 2, once the 2-amino-3-carboxamide-thiophene scaffold (iv) is isolated, introduction of the R1 group at the 2-amino position may be achieved by treating (iv) with either the corresponding primary amine in an appropriate solvent (neat amine may be used as the solvent) or the corresponding alkylating agent (exemplified by, but not limited to, the halides, the trifluoromethanesulfonate or the sulfate). Halogenation of the C5 position, using for example bromine in acetic acid in the case of bromination or thionyl chloride in the case of chlorination, affords intermediate (vi). The halogen group can be displaced, using for example Suzuki coupling conditions, to yield (vii). If necessary, the "a" substituents may be manipulated according to standard synthetic procedure, generating the desired compound (viii).

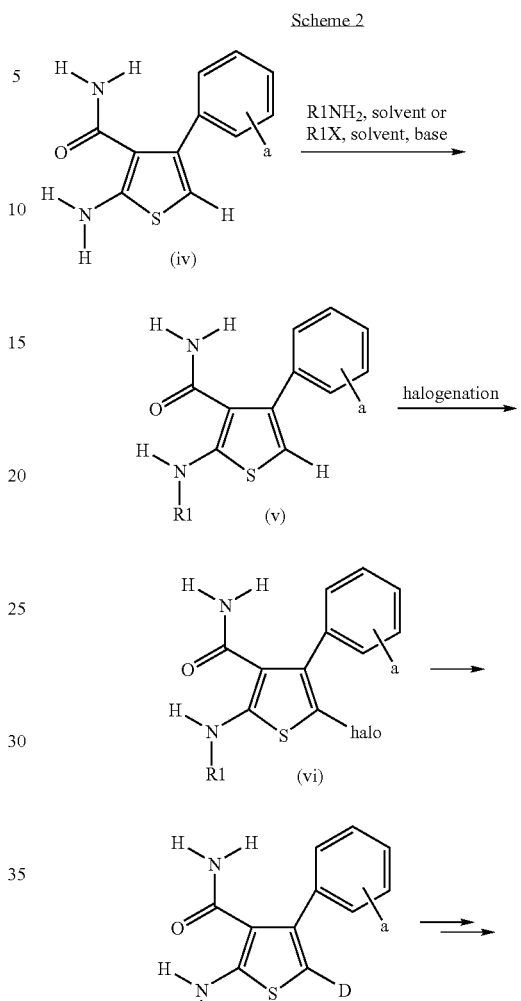

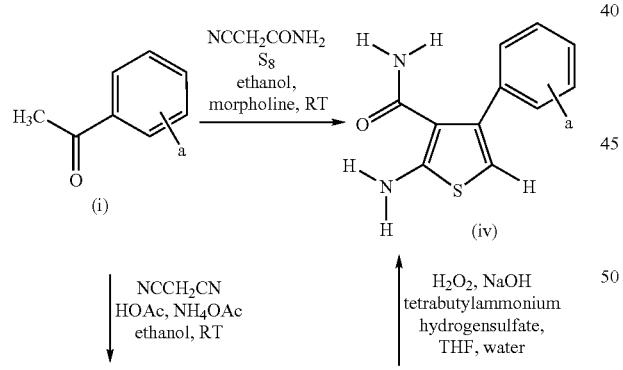

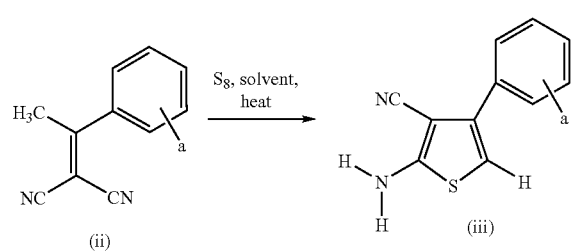

EXAMPLES

Certain embodiments of the present invention will now be illustrated by way of example only. The physical data given for the compounds exemplified is consistent with the assigned structure of those compounds.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
L (liters);
μL (microliters);
M (molar);
i. v. (intravenous);
MHz (megahertz);
mmol (millimoles);
min (minutes);
mp (melting point);
$T_r$ (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
CDI (1,1-carbonyldiimidazole);
IBCF (isobutyl chloroformate);
HOAc (acetic acid);
HOSu (N-hydroxysuccinimide);
HOBT (1-hydroxybenzotriazole);
mCPBA (meta-chloroperbenzoic acid;
EDC (ethylcarbodiimide hydrochloride);
BOC (tert-butyloxycarbonyl);
mg (milligrams);
mL (milliliters);
psi (pounds per square inch);
mM (millimolar);
Hz (Hertz);
mol (moles);
rt (room temperature);
h (hours);
TLC (thin layer chromatography);
RP (reverse phase);
i-PrOH (isopropanol);
TFA (trifluoroacetic acid);
THF (tetrahydrofuran);
AcOEt (ethyl acetate);
DCM (dichloromethane);
DMF (N,N-dimethylformamide);
FMOC (9-fluorenylmethoxycarbonyl);
DCC (dicyclohexylcarbodiimide);
CBZ (benzyloxycarbonyl);
Ac (acetyl);
TMSE (2-(trimethylsilyl)ethyl);
TIPS (triisopropylsilyl);
DMAP (4-dimethylaminopyridine);
ATP (adenosine triphosphate);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
atm (atmosphere);
TMS (trimethylsilyl);
TBS (t-butyldimethylsilyl);
BSA (bovine serum albumin)
HRP (horseradish peroxidase);
fHNO$_3$ (fumed HNO$_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR (hereinafter "NMR") spectra were recorded on a Varian VXR-300, a Varian Unity-300, a Varian Unity-400 instrument, a Brucker AVANCE-400, a Bruker AM 400 spectrometer or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% CH$_3$CN (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc; ca 50 mg of the final products were injected in 500 uL of DMSO onto a 50×20 mm I. D. YMC CombiPrep ODS-A column at 20 mL/min with a 10 min gradient from 10% CH$_3$CN (0.1% TFA) to 90% CH$_3$CN (0.1% TFA) in H$_2$O (0.1% TFA) and a 2 min hold. Flash chromatography was run over Merck Silica gel 60 (230–400 mesh).

Infrared (IR) spectra were obtained on a Nicolet 510 FT-IR spectrometer using a 1-mm NaCl cell.

Most of the reactions were monitored by thin-layer chromatography on 0.25 mm E. Merck silica gel plates (60F-254), visualized with UV light, 5% ethanolic phosphomolybdic acid or p-anisaldehyde solution.

Example 1

2-Amino-4-{4-[3-(2-fluoro-5-trifluoromethyl-phenyl)-ureido]-phenyl}-thiophene-3-carboxylic acid amide

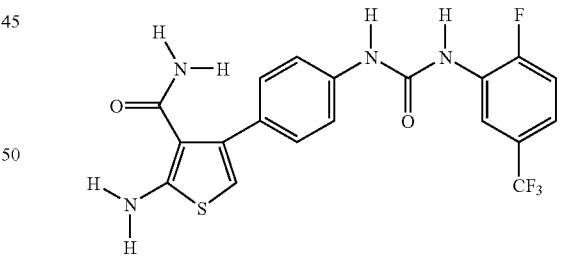

Example 1 was prepared according to procedures similar to those shown in Schemes 1 and 2.

a) 2-Amino-4-(4-nitro-phenyl)-thiophene-3-carboxylic acid amide.

Elemental sulfur (0.32 g, 10 mmoles, 1 eq), cyanoacetamide (0.84 g, 10 mmoles, 1 eq), and p-nitro-acetophenone (1.65 g, 10 mmoles, 1 eq) were ground to fine powder and treated with 2 mL ethanol and 2 mL morpholine. The slurry was stirred overnight at room temperature and poured into 20 mL methylene chloride and 25 mL brine. The organic layer was reserved and the aqueous layer was extracted with 2×15 mL methylene chloride. The organic layers were combined, dried over anhydrous sodium sulfate, filtered and concentrated to dryness. The residue was purified by flash chromatography (50% ethyl acetate-hexane) to afford 2-amino-4-(4-nitro-phenyl)-thiophene-3-carboxylic acid amide. TLC (50% ethyl acetate-hexane)=0.30. LC-MS (m/e)=264.0 (MH+). $^1$H-NMR (CDCl$_3$): ppm 6.1 (s, 1H), 7.5 (d, 2H, J=8.8 Hz), 8.2 (d, 2H, J=8.8 Hz).

b) 2-Amino-4-(4-amino-phenyl)-thiophene-3-carboxylic acid amide.

2-Amino-4-(4-nitro-phenyl)-thiophene-3-carboxylic acid amide (40 mg, 0.15 mmoles, 1 eq) was suspended in 5 mL 6M HCl solution and treated with elemental tin (96 mg, 0.80 mmoles, 5.3 eq). The reaction was complete after 15 minutes, as judged by TLC. The solution was treated with concentrated ammonium hydroxide to pH 10, and then diluted with 10 mL brine and 20 mL methylene chloride. The organic layer was reserved and the aqueous layer was washed with 2×20 mL methylene chloride. The organic layers were combined, washed with 20 mL brine, dried over solid sodium sulfate, filtered and concentrated to dryness. The crude 2-amino-4-(4-amino-phenyl)-thiophene-3-carboxylic acid amide was used as such in the next step. TLC (80% ethyl acetate-hexane)=0.52. LC-MS (m/e)=234.2 (MH+). $^1$H-NMR (CDCl$_3$): ppm 5.9 (s, 1H), 6.6 (d, 2H, J=8.0 Hz), 7.1 (d, 2H, J=8.0 Hz).

c) 2-Amino-4-{-4-[3-(2-fluoro-5-trifluoromethyl-phenyl)-ureido]-phenyl}-thiophene-3-carboxylic acid amide.

Crude 2-amino-4-(4-amino-phenyl)-thiophene-3-carboxylic acid amide (0.15 mmoles, 1 eq) was dissolved in 5 mL THF and treated with 400 μL of 0.35 M THF solution of 2-fluoro-2-trifluoromethyl-phenyl isocyanate (0.15 mmoles, 1 eq). After 1 hour, the reaction mixture was diluted with 1 mL methanol and 1 mL triethylamine, stirred for 30 minutes, and concentrated to dryness. The residue was purified by prep HPLC yielding pure 2-amino-4-{4-[3-(2-fluoro-5-trifluoromethyl-phenyl)-ureido]-phenyl}-thiophene-3-carboxylic acid amide. TLC (60% ethyl acetate)=0.35. LC-MS (m/e) =439.2 (MH+).

Example 2

2-Amino-4-[4-(3-phenyl-ureido)-phenyl]-thiophene-3-carboxylic acid amide

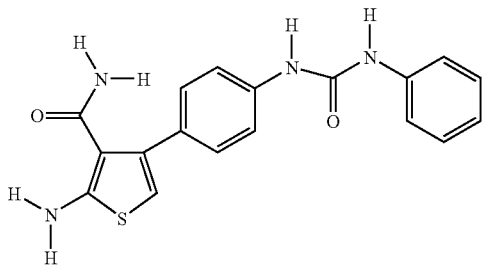

Crude 2-amino-4-(4-amino-phenyl)-thiophene-3-carboxylic acid amide (0.15 mmoles, 1 eq) is dissolved in 5 mL THF and treated with 400 μL of 0.35 M THF solution of phenyl isocyanate (0.15 mmoles, 1 eq). When the reaction is complete, as judged by TLC analysis, the reaction mixture is diluted with 1 mL methanol and 1 mL triethylamine, stirred for 30 minutes, and concentrated to dryness. The residue is purified by prep HPLC yielding pure 2-amino-4-{4-[3-phenyl-ureido]-phenyl}-thiophene-3-carboxylic acid amide.

Example 3

2-Amino-4-[4-[3-(2-chloro-5-trifluoromethyl phenyl)-ureido]-phenyl]-thiophene-3-carboxylic acid amide

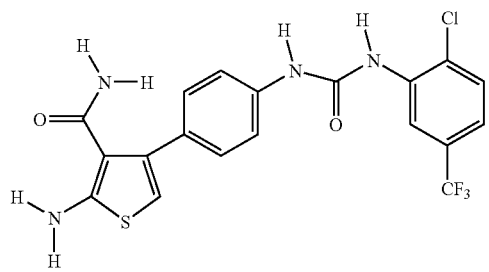

Crude 2-amino-4-(4-amino-phenyl)-thiophene-3-carboxylic acid amide (0.15 mmoles, 1 eq) is dissolved in 5 mL THF and treated with 400 μL of 0.35 M THF solution of 2-chloro-5-trifluoromethyl-phenyl isocyanate (0.15 mmoles, 1 eq). When the reaction is complete, as judged by TLC analysis, the reaction mixture is diluted with 1 mL methanol and 1 mL triethylamine, stirred for 30 minutes, and concentrated to dryness. The residue is purified by prep HPLC yielding pure 2-amino-4-{4-[3-(2-chloro-5-trifluoromethyl)-phenyl-ureido]-phenyl}-thiophene-3-carboxylic acid amide.

Example 4

2-Amino-4-[4-(3-indan-5-yl-ureido)-phenyl]-thiophene-3-carboxylic acid amide

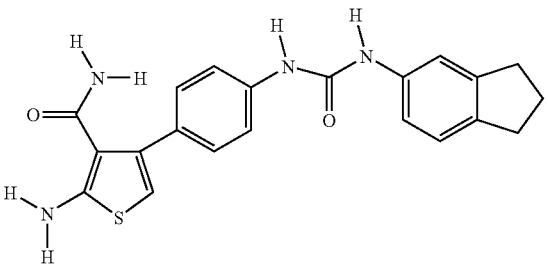

Crude 2-amino-4-(4-amino-phenyl)-thiophene-3-carboxylic acid amide (0.15 mmoles, 1 eq) is dissolved in 5 mL THF and treated with 400 μL of 0.35 M THF solution of 5-indanyl isocyanate (0.15 mmoles, 1 eq). When the reaction is complete, as judged by TLC analysis, the reaction mixture is diluted with 1 mL methanol and 1 mL triethylamine, stirred for 30 minutes, and concentrated to dryness. The residue is purified by prep HPLC yielding pure 2-amino-4-[4-(3-indan-5-yl-ureido)-phenyl]-thiophene-3-carboxylic acid amide.

Example 5

2-Amino-4-{4-[(1-[2-fluoro-5-trifluoromethyl-phenyl]-methanoyl)-amino]-phenyl}-thiophene-3-carboxylic acid amide

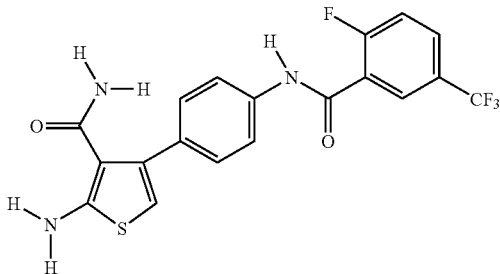

Crude 2-amino-4-(4-amino-phenyl)-thiophene-3-carboxylic acid amide (0.15 mmoles, 1 eq) is dissolved in 1 mL DMF and added to a solution of 2-fluoro-5-trifluoromethylbenzoic acid (0.20 mmoles, 1.3 equiv) and HBTU (0.20 mmoles, 1.3 equiv) in 1 mL DMF. To this solution is added 0.5 mL triethylamine. The solution is stirred at room temperature until the reaction is complete, as judged by TLC. The crude reaction mixture is purified by preparative HPLC, affording the desired 2-amino-4-{4-[(1-[2-fluoro-5-trifluoromethyl-phenyl]-methanoyl)-amino]-phenyl}-thiophene-3-carboxylic acid amide.

Biological Data

Compounds are tested for TIE-2 kinase and VEGFR kinase inhibition activity according to one or more of the following methods.

TIE-2 Enzyme Assay (TIE2-E).

The TIE-2 enzyme assay uses the LANCE method (Wallac) and GST-TIE2, baculovirus expressed recombinant constructs of the intracellular domains of human TIE2 (amino acids 762–1104, GenBank Accession # L06139) tagged by GST). The method measures the ability of the purified enzymes to catalyse the transfer of the γ-phosphate from ATP onto tyrosine residues in a biotinylated synthetic peptide, D1-15 (biotin-C6-LEARLVAYEGWVAGKKKamide). This peptide phosphorylation is detected using the following procedure: for enzyme preactivation, GST-TIE2 is incubated for 30 mins at room temperature with 2 mM ATP, 5 mM MgCl2 and 12.5 mM DTT in 22.5 mM HEPES buffer (pH7.4). Preactivated GST-TIE2 is incubated for 30 mins at room temperature in 96 well plates with 1 uM D1-15 peptide, 80 uM ATP, 10 mM MgCl2, 0.1 mg/ml BSA and the test compound (diluted from a 10 mM stock in DMSO, final DMSO concentration is 2.4%) in 1 mM HEPES (pH7.4). The reaction is stopped by the addition of EDTA (final concentration 45 mM). Streptavidin linked-APC (allophycocyanin, Molecular Probe) and Europium-labeled anti-phosphorylated tyrosine antibody (Wallac) are then added at the final concentration of 17 ug/well and 2.1 ug/well, respectively. The APC signal is measured using an ARVO multilabel counter (Wallac Berthold Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1−x/(K+x))+Y2, where "K" is equal to the $IC_{50}$. The $IC_{50}$ values are converted to $pIC_{50}$ values, i.e., −log $IC_{50}$ in Molar concentration.

TIE-2 Autophosphorykdion Assay (TIE2-C).

The TIE-2 autophosphorylation assay uses an ELISA method and a TIE2 intracellular domain/c-fms extracellular domain (TIE2/c-fms) chimeric protein expressing mouse 3T3 cells. This assay measures the autophosphorylation level of TIE2 protein expressed in cells. The cells are cultured in high glucose DMEM (Sigma) containing 10% serum at 37° C. in a humidified 10% CO2, 90% air incubator. The test compound (diluted from a 10 mM stock in DMSO, final DMSO concentration is 0.1%) is incubated with TIE2/c-fms expressing cells for 1 hr in serum free DMEM in 96 well plates followed by the activation of TIE2/c-fms receptor using c-fms ligand, MCSF (macrophage colony stimulating factor). The culture media is removed by aspiration and the cells incubated for at least 30 mins on ice with lysis buffer containing 137 mM NaCl, 2 mM EDTA, 10% glycerol, 0.09 ml sodium ortho vanadate and complete protease inhibitor cocktail (Roche) in 20 mM Tris-HCl (pH8.0). The cell extracts are transferred into Rat anti-c-fms antibody coated 96 well plates and incubated for 12 hrs at 4 degrees. The extracts are removed by aspiration and the plate is incubated with biotinylated anti-phosphotyrosine antibody, PT66 (Sigma) and then with HRP (Horseradish Peroxidase)-labeled streptavidin (PIERCE). The optical density at 450 nm derived from HRP catalyzed TMB is measured with an ARVO multilabel counter (Wallac Berthold Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1−x/(K+x))+Y2, where "K" is equal to the $IC_{50}$. The $IC_{50}$ values is converted to $pIC_{50}$ values, i.e., −log $IC_{50}$ in Molar concentration.

Tie2 Fluorescence Polarization Kinase Activity Assay (TIE2-FP).

Activation of Recombinant Tie2 Activation:

Recombinant GST-Tie2 is activated by incubating the enzyme in 20 mM Tris-HCl, pH 7.5, 12 mM $MgCl_2$, 100 mM NaCl, 20 μM sodium vanidate, 1 mM DTT and 300 μM ATP at room temperature for 2 hours. The activation mixture is then passed through a NAP-25 desalting column (Pharmacia Biotech cat. no. 17-0852-02) to remove the free ATP. The activated enzyme is stored as aliquots at −80° C. in 20 mM Tris-HCl, pH 7.5 and 100 mM NaCl.

Assay Conditions:

The final assay conditions are 50 mM HEPES, pH 7.5, 5% DMSO (when screening compounds), 200 μM ATP, 5 mM $MgCl_2$, 1 mM DTT, 50 μM sodium vanidate, 1 nM activated enzyme, and 200 μM peptide. $IC_{50}$'s of compounds are measured under subsaturating ATP (200 μM) and varing concentrations of activated Tie2 and peptide substrate (RF-WKYEFWR-OH; MW 1873 Da, TFA salt). Panvera Antiphosphotyrosine antibody (Cat#P2840) and PTK Green Tracer (Cat#P2842) are used to detect the phosphorylated peptide. Polarization is measured on a TECAN Polarion in 138-second cycles for 30 minutes at room temperature. $IC_{50}$'s are then determined from the % polarization using normal calculation methods.

2-Amino-4-{4-[3-(2-fluoro-5-trifluoromethyl-phenyl)-ureido]-phenyl}-thiophene-3-carboxylic acid amide, prepared in accordance with Example 1, was tested by the TIE2-FP assay and yielded a $pIC_{50}$ of >7.0.

VEGF-R2 Enzyme Assay (VEGF-E).

The VEGF enzyme assay uses the LANCE method (Wallac) and GST-VEGFR2, baculovirus expressed recombinant constructs of the intracellular domains of human TIE2 tagged by GST. The method measures the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation is detected using the following procedure: GST-VEGFR2 is incubated for 40–60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction is stopped by the addition of EDTA (final concentration 50 mM). Streptavidin linked-APC (allophycocyanin, Molecular Probe) and Europium-labeled anti-phosphorylated tyrosine antibody (Wallac) are then added at the final concentration of 15 nM and 1 nM, respectively. The APC signal is measured using an ARVO multilabel counter (Wallac Berthold, Japan). The percent inhibition of activity is calculated relative to blank control wells. The concentration of test compound that inhibits 50% of activity ($IC_{50}$) is interpolated using nonlinear regression (Levernberg-Marquardt) and the equation, y=Vmax (1−x/(K+x))+Y2, where "K" is equal to the $IC_{50}$. The $IC_{50}$ values are converted to $pIC_{50}$ values, i.e., −log $IC_{50}$ in Molar concentration.

VEGF-Driven Cellular Proliferation Assay: BrdU Incorporation Assay (VEGF-C).

Human umbilical cord endothelial cells (HUVEC, Clonetics, CC2519) are passaged in Type I collagen-coated 100-mm petridishes in EGM-MV medium (Clonetics, CC3125) at 37 C in a humidified 5% CO2, 95% air incubator. (HUVEC passaged more than 6 times in vitro are discarded and not subjected to assaying.) The cells are harvested using trypsin/EDTA, counted using a haemocytometer and plated at 5000 cells/well in a Type I-collagen coated 96-well plate (Becton Dickinson, 354407) in M199 medium (Gibco BRL, 12340-030) containing 5% FBS (Hyclone, A 1115-L) and gentamicin (at 50 ug/ml, Gibco BRL). After incubation overnight at 37° C., the media are replaced with 100 ul of M199 serum-free medium containing compounds at various concentrations with 0.6% DMSO and gentamicin. The compounds are diluted in serum-free M199 medium from 10 mM stock solutions prepared in 100% DMSO. After a 30 min incubation at 37° C., the cells are fed with 100 ul of serum-free M199 medium containing gentamicin, 0.2% culture-grade bovine serum albumin (BSA, Sigma A1993) and 20 ng/ml of VEGF (R&D systems, 293-VE) or 0.6 ng/ml of basic FGF (R&D systems, 233-FB), and cultured at 37° C. for another 24 h. The cells are pulsed with bromodeoxyuridine (BrdU at 10 uM in serum-free M199) at 37° C. for an additional 24 h. The incorporation of BrdU into the proliferating HUVEC is analyzed using BrdU Cell Proliferation ELISA (Roche Molecular Biochemicals, 1647229) according to the manufacturer's protocols. The optical density at 450 nm is measured with a multilabel counter (ARVO SX, Wallac). The percent inhibition of cell growth is calculated relative to blank control wells. The concentration of test compound that inhibits 50% of cell growth ($IC_{50}$) is interpolated using nonlinear regression (Levernberg-Marquardt) and the equation, y=Vmax (1−x/(K+x))+Y2, where "K" is equal to the $IC_{50}$. The $IC_{50}$ values are converted to $pIC_{50}$ values, i.e., −log $IC_{50}$ in Molar concentration.

What is claimed is:
1. A compound of Formula (I):

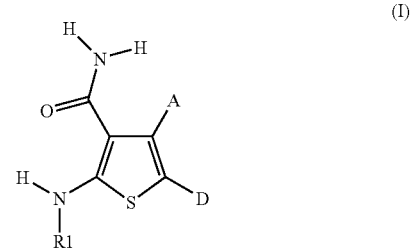

wherein:
A is aryl, heteroaryl, heterocyclyl, —$RR^3$, —$C(O)OR^4$, —$C(O)NR^5R^6$, or —$C(O)R^4$, wherein the aryl, heteroaryl, and heterocyclyl may optionally be substituted;

D is hydrogen, $C_1$–$C_6$ alkyl, halo, aryl, heteroaryl, heterocyclyl, —$RR^3$, —$C(O)OR^4$, —$C(O)NR^5R^6$, or —$C(O)R^4$, wherein the alkyl, aryl, heteroaryl, and heterocyclyl may optionally be substituted;

R is independently selected from $C_1$–$C_6$ alkylene, $C_2$–$C_6$ alkenylene, or $C_2$–$C_6$ alkynylene, wherein the alkylene, alkenylene, and alkynylene may optionally be substituted;

$R^1$ is hydrogen, $C_1$–$C_6$ alkyl, $C_3$–$C_7$ cycloalkyl, $C_1$–$C_6$ alkoxy, $C_3$–$C_7$ cycloalkoxy, aryl, heteroaryl, aralkyl, aryloxy, heterocyclyl, —$C(O)OR^7$, or —$C(O)NR^7R^7$, where both $R^7$ are not simultaneously H, and wherein the alkyl, cycloalkyl, alkoxy, cycloalkoxy, aryl, heteroaryl, aralkyl, aryloxy and heterocyclyl may optionally be substituted;

$R^3$ is independently selected from halo, $C_1$–$C_6$ alkyl, $C_3$–$C_7$ cycloalkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —$NHC(O)R^4$, —$NHC(S)R^4$, —$NR^5R^6$, $RNR^5R^6$, —$SR^4$, —$S(O)_2R^4$, —$RC(O)OR^4$, —$C(O)OR^4$, —$C(O)R^4$, —$C(O)NR^5R^6$, —$NHS(O)_2R^4$, —$S(O)_2NR^5R^6$, or —$NHC(=NH)R^4$; wherein the alkyl, cycloalkyl, haloalkyl, alkoxy, cycloalkoxy, haloalkoxy, aryl, aralkyl, aryloxy, heteroaryl, and heterocyclyl may optionally be substituted;

$R^4$ is independently selected from hydrogen, $C_1$–$C_6$ alkyl, aryl, heteroaryl, heterocyclyl, —$RR^3$, —NR'''R'''', or —NR'NR'''R''''; wherein the alkyl, aryl, heteroaryl, and heterocyclyl may optionally be substituted;

$R^5$ is independently selected from hydrogen, $C_1$–$C_6$ alkyl, $C_3$–$C_7$ cycloalkyl, cyanoalkyl, —R'R'', aryl, aralkyl, heteroaryl, —NHC(O)OR''', —R'NHC(O)OR''', —R'NHC(O)NR'''R'''', or —R'C(O)OR'''; wherein the alkyl, cycloalkyl, cyanoalkyl, aryl, aralkyl, and heteroaryl may optionally be substituted;

$R^6$ is independently selected from hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R'''; wherein the alkyl, cycloalkyl, cyanoalkyl, aryl, aralkyl, and heteroaryl may optionally be substituted;

$R^7$ is independently selected from hydrogen, $C_1$–$C_6$ alkyl, or aryl, wherein the alkyl and aryl may optionally be substituted;

R' is independently selected from optionally substituted $C_1$–$C_3$ alkylene;

R' is independently selected from optionally substituted heteroalkyl or NR'''R'''';

R" is independently selected from hydrogen, $C_1$–$C_6$ alkyl, aryl, aralkyl, heteroaryl, or $C_3$–$C_7$ cycloalkyl; wherein the alkyl, aryl, aralkyl, heteroaryl, and cycloalkyl may optionally be substituted; and R"" is independently selected from hydrogen, $C_1$–$C_6$ alkyl, aryl, heteroaryl, or $C_3$–$C_7$ cycloalkyl; wherein the alkyl, aryl, heteroaryl, and cycloalkyl may optionally be substituted;

or a salt, solvate, or physiologically functional derivative thereof.

2. A compound as claimed in claim 1, wherein A is aryl substituted with at least one independently selected $R^3$ group and optionally further substituted; or a salt, solvate, or physiologically functional derivative thereof.

3. A compound as claimed in claim 2, wherein $R^1$ is hydrogen; or a salt, solvate, or physiologically functional derivative thereof.

4. A compound as claimed in claim 3, wherein D is hydrogen; or a salt, solvate, or physiologically functional derivative thereof.

5. A compound as claimed in claim 1, wherein:
A is aryl substituted with at least one independently selected $R^3$ and optionally further substituted;
$R^3$ is —NHC(O)$R^4$;
$R^4$ is —NR'"R"";
$R^3$ and $R^4$ optionally substituted as valency permits;
$R^1$ is hydrogen; and
D is hydrogen;
or a salt, solvate, or physiologically functional derivative thereof.

6. A compound as claimed in claim 5, wherein:
A is phenyl substituted with at least one independently selected $R^3$ group and optionally further substituted;
$R^3$ is —NHC(O)$R^4$;
$R^4$ is —NR'"R"";
R'" is hydrogen;
R"" is optionally substituted aryl;
$R^3$, $R^4$, and R"" being optionally substituted as valency permits;
$R^1$ is hydrogen; and
D is hydrogen;
or a salt, solvate, or physiologically functional derivative thereof.

7. A compound as claimed in claim 1, selected from the group consisting of:
2-Amino-4-{4-[3-(2-fluoro-5-trifluoromethyl-phenyl)-ureido]-phenyl}-thiophene-3-carboxylic acid amide;
2-Amino-4-[4-(3-phenyl-ureido)-phenyl]-thiophene-3-carboxylic acid amide;
2-Amino-4-[4-[3-(2-chloro-5-trifluoromethyl)-phenyl-ureido]-phenyl]-thiophene-3-carboxylic acid amide;
2-Amino-4-[4-(3-indan-5-yl-ureido)-phenyl]-thiophene-3-carboxylic acid amide; and
2-Amino-4-{4-[(1-[2-fluoro-5-trifluoromethyl-phenyl]-methanoyl)-amino]-phenyl}-thiophene-3-carboxylic acid amide;
or a salt, solvate, or physiologically functional derivative thereof.

8. A pharmaceutical composition, comprising: a therapeutically effective amount of a compound as claimed in claim 1, or a salt, solvate, or a physiologically functional derivative thereof, and one or more of pharmaceutically acceptable carriers, diluents and excipients; the composition optionally further comprising an additional agent which is an antineoplastic agent, and/or an agent which inhibits angiogenesis.

9. A method of treating cancer in a mammal, comprising: administering to said mammal a therapeutically effective amount of a compound as claimed in claim 1, or a salt, solvate, or a physiologically functional derivative thereof, the method optionally further comprising administering a therapeutically effective amount of at least one additional anti-cancer therapy, concomitantly with, before, and/or after the administration of the compound, salt, solvate or physiologically functional derivative as claimed in claim 1.

10. A compound as claimed in claim 1, wherein:
A is aryl or heteroaryl optionally substituted with at least one independently selected $R^3$ group and optionally further substituted.

11. A compound as claimed in claim 1, wherein:
D is aryl or heteroaryl optionally substituted with at least one independently selected $R^3$ group and optionally further substituted.

12. A compound as claimed in claim 1, wherein:
$R^1$ is aryl or heteroaryl optionally substituted with at least one independently selected $R^3$ group and optionally further substituted.

13. A method as claimed in claim 9, further comprising administering a therapeutically effective amount of the at least one additional anti-cancer therapy, concomitantly with, before, and/or after the administration of the compound, salt, solvate or physiologically functional derivative as claimed in claim 1.

* * * * *